US008814799B2

(12) United States Patent
Zelenka et al.

(10) Patent No.: US 8,814,799 B2
(45) Date of Patent: *Aug. 26, 2014

(54) LOW PROFILE INTRAVASCULAR ULTRASOUND CATHETER

(75) Inventors: Robert Zelenka, Milpitas, CA (US); Daniel Okeeffe, San Francisco, CA (US); Mikael Cars, Campbell, CA (US); Bruce McEvers, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/612,302

(22) Filed: Sep. 12, 2012

(65) Prior Publication Data

US 2013/0023771 A1      Jan. 24, 2013

Related U.S. Application Data

(63) Continuation of application No. 11/963,596, filed on Dec. 21, 2007, now Pat. No. 8,277,381.

(51) Int. Cl.
*A61M 25/00* (2006.01)
*A61B 8/12* (2006.01)
*A61B 8/00* (2006.01)
*A61M 25/01* (2006.01)

(52) U.S. Cl.
CPC ........ *A61B 8/4461* (2013.01); *A61M 2025/018* (2013.01); *A61M 2025/0059* (2013.01); *A61B 8/12* (2013.01); *A61B 8/4483* (2013.01); *A61B 8/445* (2013.01); *A61M 25/0054* (2013.01); *A61M 2025/0175* (2013.01); *A61M 2025/0042* (2013.01); *A61M 2025/0183* (2013.01); *A61M 2025/0098* (2013.01)
USPC ................... 600/459; 604/164.13; 604/533

(58) Field of Classification Search
USPC .......... 600/459–465, 481; 604/93.01, 103.03, 604/103.09, 164.13, 533–535, 538
See application file for complete search history.

(56) References Cited

U.S. PATENT DOCUMENTS 4,564,014 A    1/1986  Fogarty et al.
5,243,988 A    9/1993  Sieben et al.
(Continued)

FOREIGN PATENT DOCUMENTS

EP    0557127 A2    8/1993
EP    0835634 A1    4/1998
(Continued)

OTHER PUBLICATIONS

Official Communication, U.S. Appl. No. 11/963,596, mailed May 11, 2011.

(Continued)

*Primary Examiner* — Parikha Mehta
(74) *Attorney, Agent, or Firm* — Lowe Graham Jones PLLC; Bruce E. Black

(57) ABSTRACT

The present invention provides low profile intravascular ultrasound catheters adapted to access sites within the patient's body through narrow blood vessels, e.g., the radial artery. In an embodiment, a low profile catheter comprises an catheter sheath, a short guidewire receiver attached to the distal end of the catheter sheath, and a telescope assembly at the proximal end. The catheter sheath comprises a main portion and a tapered portion for increased flexibility toward the distal end of the catheter. In one embodiment, a rotatable and translatable imaging core is received within the catheter sheath for ultrasound imaging. A short guidewire receiver is used to allow the imaging core to be advanced farther distally with respect to the distal end of the catheter. In an embodiment, the catheter sheath extends through a portion of the telescope assembly to provide enhanced support of the imaging core within the telescope assembly.

19 Claims, 6 Drawing Sheets

(56) References Cited

U.S. PATENT DOCUMENTS

| | | | |
|---|---|---|---|
| 5,342,386 | A | 8/1994 | Trotta |
| 5,353,798 | A | 10/1994 | Sieben |
| 5,400,789 | A | 3/1995 | Griffith |
| 5,438,997 | A | 8/1995 | Sieben et al. |
| 5,445,155 | A | 8/1995 | Sieben |
| 5,464,016 | A | 11/1995 | Nicholas et al. |
| 5,582,171 | A | 12/1996 | Chornenky et al. |
| 5,722,402 | A | 3/1998 | Swanson et al. |
| 5,740,808 | A | 4/1998 | Panescu et al. |
| 5,876,336 | A | 3/1999 | Swanson et al. |
| 5,941,251 | A | 8/1999 | Panescu et al. |
| 6,070,094 | A | 5/2000 | Swanson et al. |
| 6,095,150 | A | 8/2000 | Panescu et al. |
| 6,353,751 | B1 | 3/2002 | Swanson et al. |
| 6,398,755 | B1 | 6/2002 | Belef et al. |
| 6,456,864 | B1 | 9/2002 | Swanson et al. |
| 6,516,807 | B1 | 2/2003 | Panescu et al. |
| 7,155,272 | B2 | 12/2006 | Yamaguchi et al. |
| 7,156,816 | B2 | 1/2007 | Schwartz et al. |
| 2005/0113631 | A1 | 5/2005 | Bolling et al. |
| 2005/0177068 | A1 | 8/2005 | Simpson |
| 2006/0264800 | A1 | 11/2006 | Bolling et al. |
| 2006/0264801 | A1 | 11/2006 | Bolling et al. |
| 2006/0270963 | A1 | 11/2006 | Bolling et al. |
| 2006/0270966 | A1 | 11/2006 | Bolling et al. |
| 2006/0276682 | A1 | 12/2006 | Bolling et al. |

FOREIGN PATENT DOCUMENTS

| | | |
|---|---|---|
| EP | 1424100 A1 | 6/2004 |
| WO | 9216147 A1 | 10/1992 |
| WO | 9427501 A1 | 12/1994 |
| WO | 9427502 A1 | 12/1994 |
| WO | 9819619 A1 | 5/1998 |
| WO | 2005046779 A2 | 5/2005 |
| WO | 2008086376 A2 | 7/2008 |

OTHER PUBLICATIONS

Official Communication, U.S. Appl. No. 11/963,596, mailed Oct. 24, 2011.

Official Communication, U.S. Appl. No. 11/963,596, mailed Jan. 6, 2012.

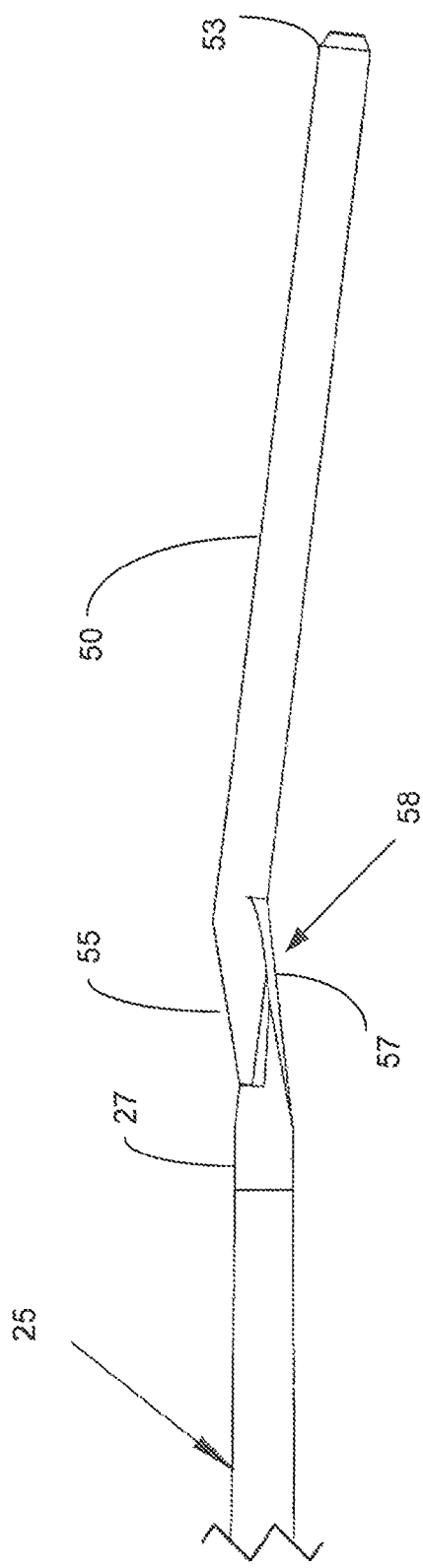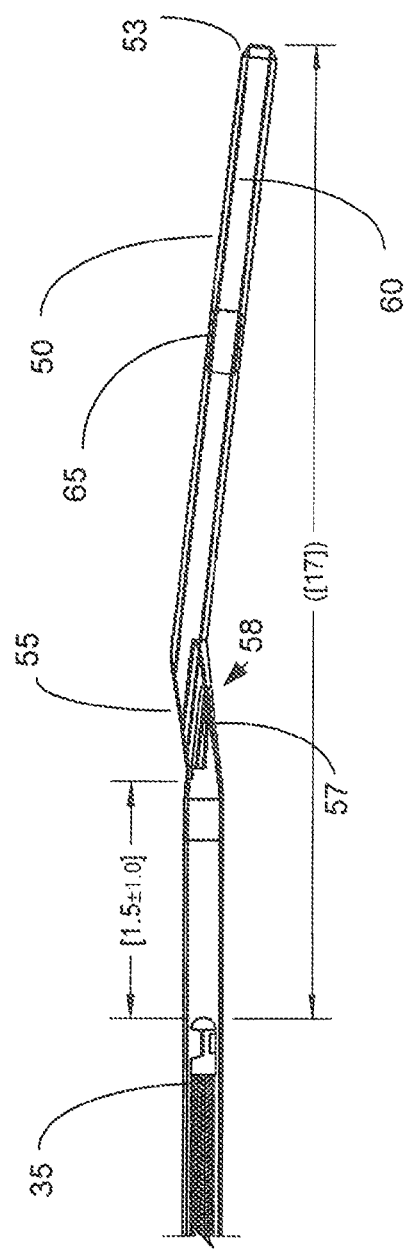

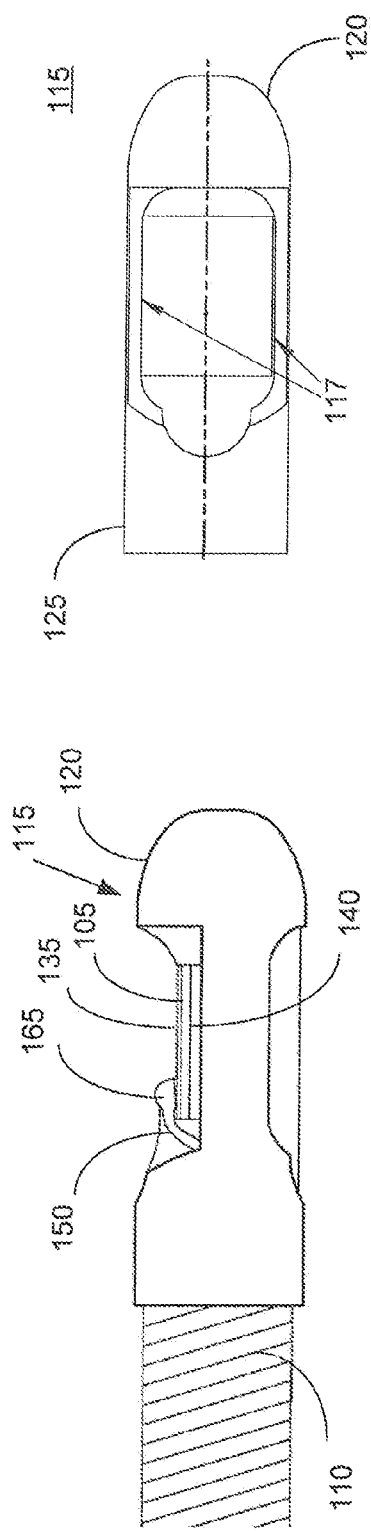
FIG. 4
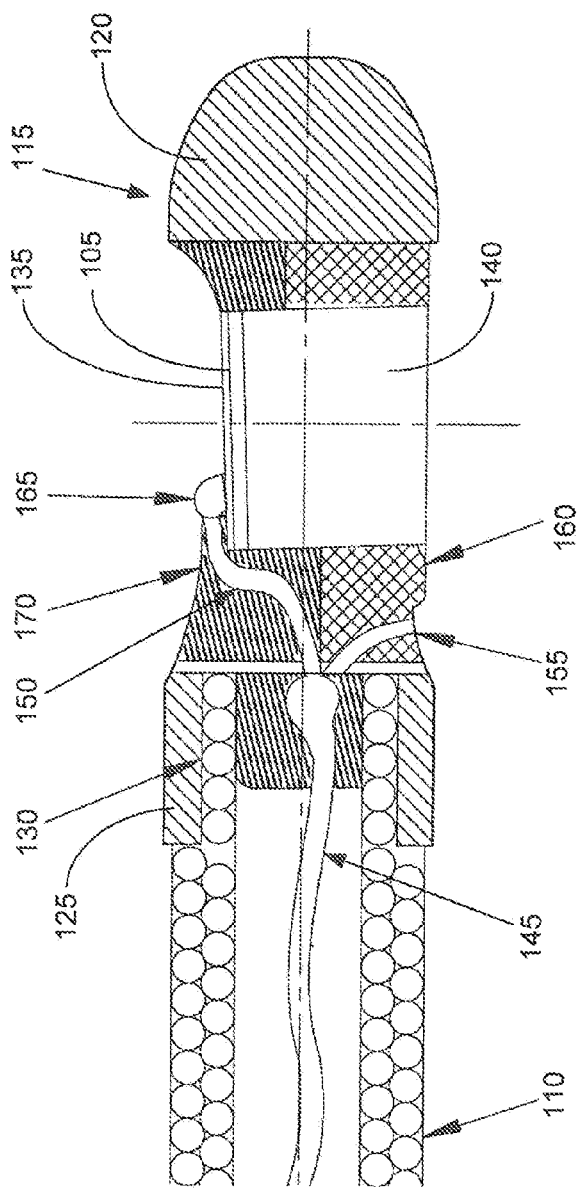
FIG. 5
FIG. 6

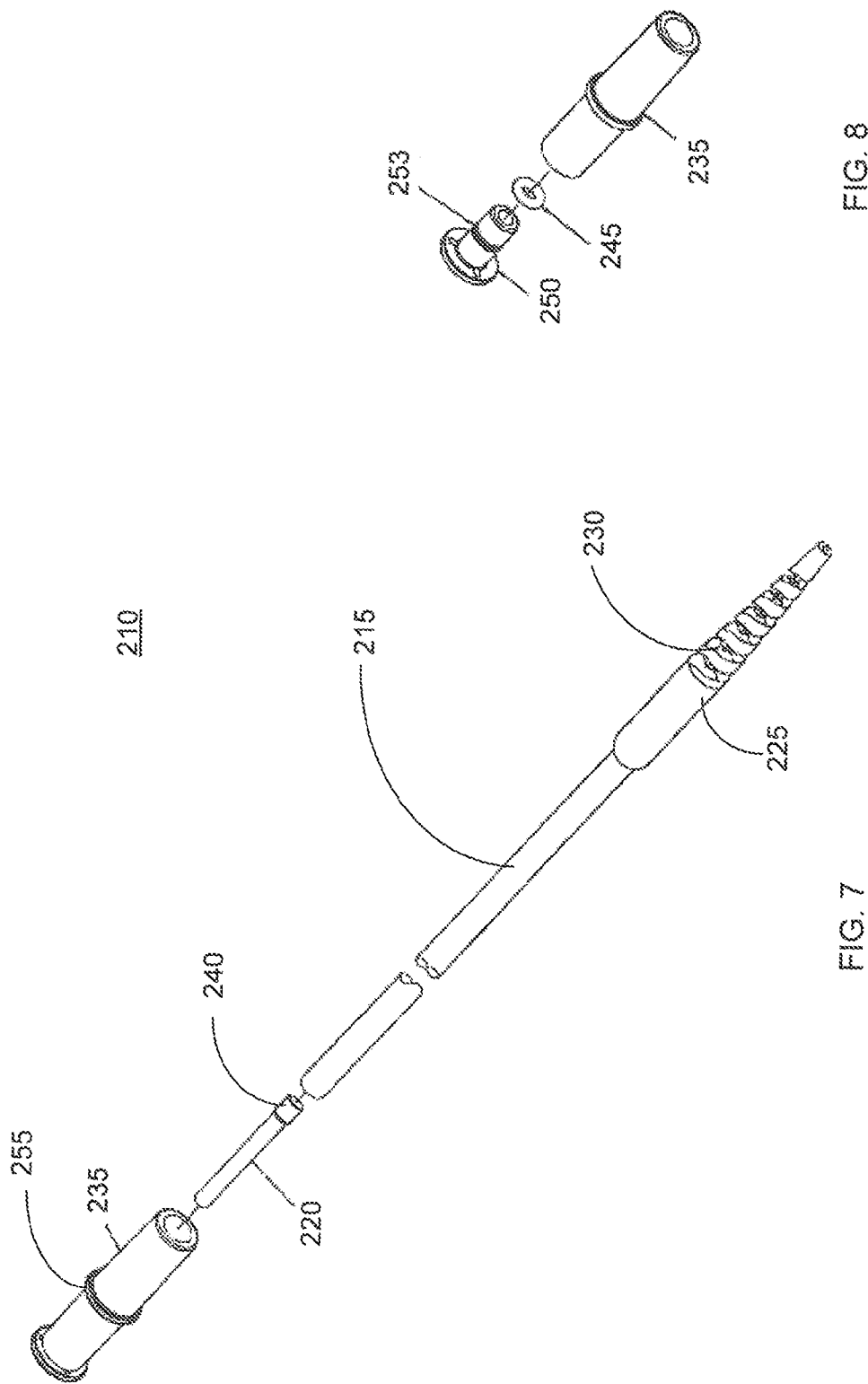

LOW PROFILE INTRAVASCULAR ULTRASOUND CATHETER

CROSS-REFERENCE TO RELATED APPLICATIONS

This patent application is a continuation of U.S. patent application Ser. No. 11/963,596, filed Dec. 21, 2007, now U.S. Pat. No. 8,277,381, which is incorporated herein by reference.

FIELD OF THE INVENTION

The present invention relates to catheters, and more particularly to low profile intravascular catheters.

BACKGROUND INFORMATION

Intravascular ultrasound imaging systems (IVUS) are used to obtain ultrasound images inside a patient's body. An IVUS system typically includes an ultrasound catheter having a flexible catheter sheath adapted for insertion into the vascular system of the patient. To obtain ultrasound images, the catheter comprises an imaging core received within a lumen of the catheter sheath. The imaging core comprises an ultrasound transducer connected to the distal end of a flexible drive cable that extends to the proximal end of the catheter through the catheter lumen. The drive cable is used to rotate and longitudinally translate the transducer within the catheter lumen to obtain images at different positions within the patient's body.

An IVUS catheter is commonly advanced through a guide catheter to a desired site within the patient's body. A problem with existing catheters is that they are adapted for use with guide catheters that are 6 French or greater in diameter. As a result, these catheters can not be used to access desired sites within the patient's body through narrower blood vessels, e.g., the radial artery, without risk of vessel spasm.

Therefore, there is a need for a low profile intravascular catheter that can be used with guide catheters that are 5 French or smaller in diameter. Such a catheter would allow easier access to sites within the patient's body through the radial artery.

SUMMARY OF THE INVENTION

The present invention provides low profile intravascular ultrasound catheters adapted to access sites within the patient's body through narrow blood vessels, e.g., the radial artery.

In a preferred embodiment, a low profile intravascular catheter is adapted to navigate through a guide catheter that is 5 French (approximately 0.066 inch) or smaller in diameter. This allows the catheter to more easily access sites within the vascular system (e.g., coronary vessel) through the radial artery.

In an exemplary embodiment, a low profile catheter comprises an elongated catheter sheath, a short guidewire receiver attached to the distal end of the catheter sheath, and a telescope assembly at the proximal end of the catheter sheath. The catheter sheath comprises a main portion and a tapered portion located distally to the main portion. The tapered portion has an outer diameter and wall thickness that gradually decreases along the length of the tapered portion toward the distal end of the catheter. The tapered portion provides increased flexibility toward the distal end of the catheter enhancing the catheter's ability to navigate the tortuous path of a blood vessel and facilitating lesion crossibility. The tapered portion also provides a gradual increase in stiffness toward the main portion of the catheter sheath for increased pushability of the catheter through the blood vessel.

In one embodiment, a rotatable and translatable imaging core is received within a lumen of the catheter sheath for obtaining ultrasound images at different positions within the patient's body. In an embodiment, the imaging core comprises an ultrasound transducer with a rectangular face to maximize the ultrasound emitting surface area of the transducer with respect to the catheter size. In another embodiment, the length of the guidewire receiver attached to the distal end of the sheath is kept short to allow the imaging core to be advanced farther distally with respect to the distal end of the catheter.

In one embodiment, the catheter comprises a telescope assembly at the proximal end of the catheter sheath. The telescope comprises a female telescoping tube and a male telescoping tube adapted to slid within the female telescoping tube to retract and extend the telescope assembly. In an embodiment, the catheter sheath extends through the female telescoping tube to provide enhanced support for the imaging core within the female telescoping tube.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

In order to better appreciate how the above-recited and other advantages and objects of the present inventions are objected, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed, attributes may be illustrated schematically rather than literally or precisely.

FIG. 2 shows a close up view of the distal portion of the catheter according to an example embodiment of the present invention.

FIG. 3 shows a cross-sectional view of the distal portion of the catheter including an imaging core according to an example embodiment of the present invention.

FIG. 4 shows a close up view of the distal portion of the imaging core according to an example embodiment of the present invention.

FIG. 5 shows a top view of a transducer housing according to an example embodiment of the present invention.

FIG. 6 shows a cross-sectional view of the distal portion of the imaging core according to an example embodiment of the invention.

FIGS. 7 and 8 show exploded views of a telescope assembly according to an example embodiment of the present invention.

DETAILED DESCRIPTION

Figure 1:
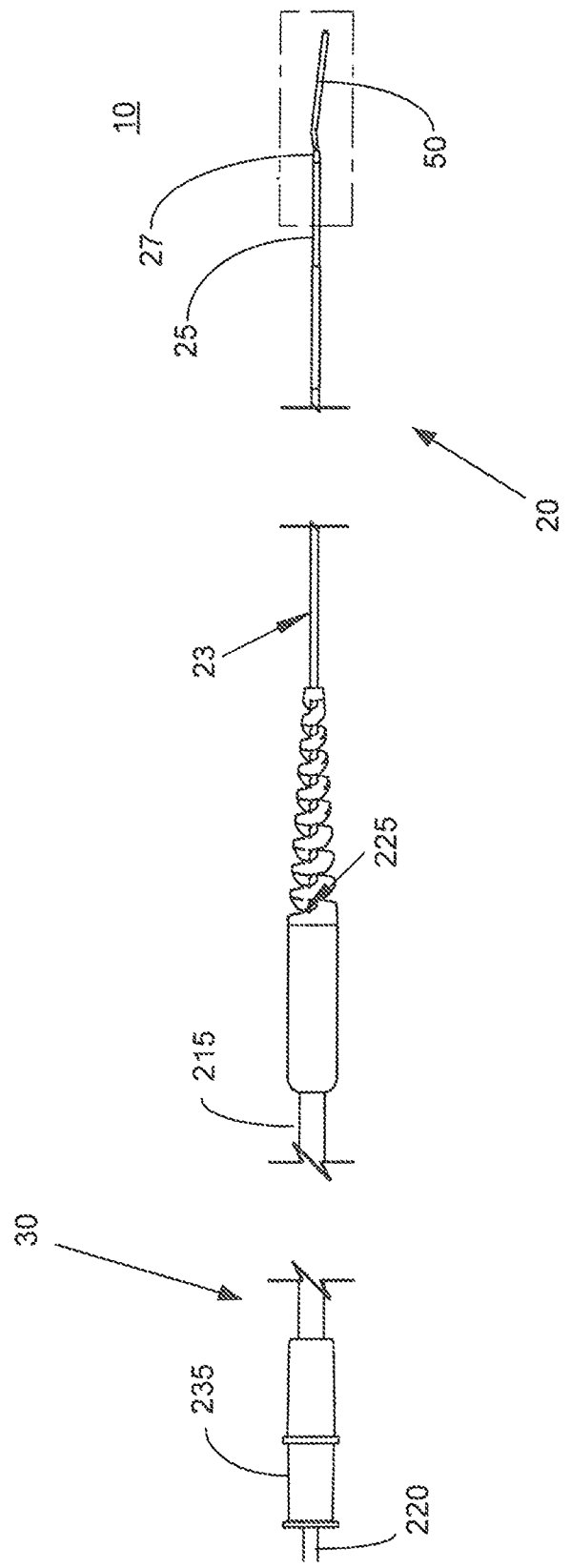
FIG. 1 shows a low profile catheter according to an example embodiment of the present invention.

FIG. 1 shows a low profile intravascular ultrasound catheter 10 according to an embodiment of the present invention. The low profile ultrasound catheter 10 is adapted access sites within the patient's body through narrow blood vessels, e.g., the radial artery. In the preferred embodiment, the sheath 20 of the catheter 10 is adapted to navigate through a guide catheter that is 5 French (approximately 0.066 inch) or smaller in diameter. Thus, the low profile catheter 10 is preferably 5 French compliant. This allows the catheter 10 to more easily access sites within the vascular system (e.g., coronary vessel) through the radial artery. Access through the radial artery provides for greater patient comfort during a follow up procedure, in which an area of the vascular system that has undergone an operation is examined post operation.

The catheter 10 comprises an elongated catheter sheath 20 having a distal portion 27, a tapered portion 25, and a main portion 23. The catheter sheath 20 may be coated with a lubricious coating to facilitate movement of the sheath 20. The tapered portion 25 is located distally from the main portion 23 of the catheter sheath 20 to provide increased flexibility of the catheter sheath 10 toward the distal end. The catheter 10 also includes a short guidewire receiver 50 attached to the distal end of the catheter sheath 20 for receiving a guidewire (not shown). The guidewire receiver comprise a guidewire rail with a lumen adapted to receive the guidewire. Further, the catheter 10 includes a telescope assembly 30 at its proximal end for translating an imaging core (shown in FIG. 3) longitudinally within the catheter sheath 20.

FIGS. 2 and 3 show the distal portion of the catheter 10. As shown in FIG. 3, the catheter sheath 20 has a lumen for receiving an imaging core 35. The imaging core 35 is able to rotate and translate longitudinally within the lumen of the catheter sheath 20 for imaging the interior of the patient. The imaging core 35 is described in greater detail below.

The main portion 23 of the catheter sheath 20 preferably has a wall thickness that is thick enough to provide pushability for the catheter 10, where pushability is the ability of the catheter to transmit a pushing force applied to its proximal end so that the catheter can be pushed through a blood vessel from the proximal end. In an embodiment, the main portion of the catheter sheath has an outer diameter of approximately 0.039 inches and wall thickness of approximately 0.006 inches, and an effective length of approximately 135 cm. The outer diameter is preferably less than 0.045 inches for 5 French compliance.

The tapered portion 25 of the catheter sheath 20 has an outer diameter and wall thickness that gradually decreases along the length of the tapered portion 25 in the direction from the main portion 23 to the distal portion 27 of the sheath 20. In an exemplary embodiment, the tapered portion 25 has an outer diameter of 0.039 inches and a wall thickness of 0.006 inches at its proximal end that tapers down to an outer diameter of 0.033" inches and a wall thickness of 0.003 inches at its distal end. The tapered portion 25 has a length of between 10 cm and 20 cm. The tapered portion 25 increases the flexibility of the catheter 10 toward the distal end, enhancing the catheter's 10 ability to navigate the tortuous path of a blood vessel. The distal portion 27 of the catheter sheath has an outer diameter of 0.033 inches, a wall thickness of 0.003 inches, and a length of about 2.5 cm.

The sheath may be made of a variety of polymeric materials, such as polytetrafluoroethylene (PTFE), polyethylene, PEEK, PEBAX or the like. In one embodiment, the main portion 23, tapered portion 25, an distal portion 27 of the catheter sheath are separate polymer tubes that are bonded together to form the catheter sheath 20. The main portion 23 and tapered portion 25 may be bonded together. For example, the two portions may be bonded together by an adhesive and then heated to fuse the two portions together (e.g., in a reflow process). The tapered portion 25 and distal portion 27 may be bonded in a similar manner. The tapered portion 25 may be fabricated using an extrusion process to gradually decrease the outer diameter and wall thickness of the tapered portion 25 along its length.

FIGS. 2 and 3 show the short guidewire receiver 50 attached to the distal end of the catheter sheath 20. The guidewire receiver 50 preferably comprises an elastomeric material with a lubricious liner. For example, the guidewire receiver 50 may be made of ethylene vinyl acetate (EVA) with a Teflon liner. During operation, a guidewire (not shown) is advanced through a blood vessel to a desired site. The proximal end of the guidewire is then threaded through the guidewire receiver 50 to guide the catheter 10 to the desired site. The length of the guidewire receiver 50 is kept short to provide greater distal access for the imaging core 35 within the catheter sheath 20. Keeping the length of the guidewire receiver 50 short allows the imaging core 35 to be advanced farther distally. In one embodiment, the guidewire receiver 50 has a length of 13 millimeters. Preferably, the receiver 50 is less than 20 millimeters in length. In FIG. 3 the unit of measurement inside the brackets is millimeters.

FIG. 3 shows a close up cross-sectional view of the short guidewire receiver 50. The guidewire receiver 50 has a lumen 60, a distal opening for receiving the guidewire, and proximal opening for the guidewire to exit the guidewire receiver 50. In an exemplary embodiment, the lumen 60 has a diameter of 0.016 inches. The distal tip 53 of the guidewire receiver 50 has a beveled shape or chamfer to enhance the crossibility of the catheter 10, where crossibility is the ability of the catheter 10 to move across the surface of a narrow passage. The distal tip 53 may have other shapes to enhance crossibility, e.g., curved surface. The guidewire receiver 50 may also include a radio opaque marker 65 for providing fluoroscopic guidance of the catheter 10. Preferably, the guidewire receiver 50 has an outer diameter of less than 0.045 inches.

In the exemplary embodiment shown in FIGS. 2 and 3, the guidewire receiver 50 is attached to the catheter sheath 20 at an angle to the longitudinal axis of the catheter sheath 20. The angles may be 6 degrees, preferably less than 10 degrees. The proximal portion 55 of the guidewire receiver 50 attached to the catheter sheath 20 tapers downward and the portion 57 of the catheter sheath 20 attached to the guidewire receiver 50 tapers upward. This tapering of the guidewire receiver 50 and the catheter sheath 20 maintains the low profile of the catheter 10 throughout the region 58 where the guidewire receiver 50 attaches to the catheter sheath 20. The proximal portion 55 of the guidewire receiver 50 and the portion 57 of the catheter sheath 20 may be bonded together, e.g., by heat bonding. Heat applied during the bonding process may be used to reshape the portion 57 of the catheter sheath 20 attached to the guidewire receiver 50 from a generally cylindrical shape to the shape shown in FIGS. 2 and 3. This may be done, e.g., by applying heat to soften the catheter sheath 20 and using a clamp to reshape the softened sheath into the desired shape.

FIGS. 4-6 show an exemplary imaging core 35 that can be received in the catheter sheath 20 for ultrasound imaging. Preferably, the portion of the sheath 20 from which the imaging core 35 images is acoustically transparent to allow for the transmission of ultrasound waves through the sheath 20. The imaging core 35 comprises an ultrasound transducer 105, e.g., a piezoelectric crystal (PZT), connected to the distal end of a drive cable 110, which extends through the lumen of the catheter sheath 20. The drive cable 110 is used to rotate and translate the transducer 105 within the catheter sheath 20. The drive cable 110 preferably possesses a high torsional stiffness so that the drive cable 110 can transmit torque from a drive motor (not shown) to the transducer to rotate the transducer 105. The drive cable 110 also possesses a low bending stiffness allowing the drive to bend along a tortuous path of a blood vessel. For example, the drive cable 100 may comprise two counterwound coils.

FIG. 6 show a cross-sectional view of the distal portion of the imaging core 35. The imaging core 35 comprises a transducer housing 115 attached to the distal end of the drive cable 20. The transducer housing 115 may be made of steel, and has a curved tip 120 to facilitate forward movement of the imaging core 35 in the catheter sheath 20 lumen. The transducer housing 115 also has a space for receiving the transducer, and an attachment portion 125 for attaching the transducer housing 115 to the drive cable 110. In this embodiment, the attachment portion 125 has a generally cylindrical shape and fits around a distal portion 130 of the drive cable 125 and is bonded to the drive cable 110 by solder.

The imaging core 35 further comprises a transducer assembly housed within the transducer housing 115. The transducer assembly comprises the transducer 105, e.g., PZT, a matching layer 135 on top of the transducer 105 and a backing layer 140 on the bottom of the transducer 105. The matching layer 135 provides acoustic matching between the transducer 105 and the surrounding fluid. The backing layer 140 is made of an acoustically absorbent material to direct emissions of ultrasound waves from the top of the transducer 105. In this exemplary embodiment, the transducer 105 has a rectangular face to maximize the ultrasound emitting surface area of the transducer 105 relative to the size of the housing 115. This improves both the transducer 105 output and sensitivity while maintaining a low profile. The transducer 105 may be tilted at a slight angle so that ultrasound waves are emitted at a slight angle relative to the perpendicular direction. This is done so that ultrasound waves that are reflected off the catheter sheath 20 are not directed back to the transducer 105.

The imaging core 35 further comprises a twisted pair wire 145 running through a central lumen in the drive cable 110. The twisted pair wire 145 provides electrical communication between the transducer 105 and the proximal end of the drive cable 110, which is electrically coupled to ultrasound electronics (not shown), e.g., by an inductive coupler, slip rings or the like. The twisted pair wire 145 comprises a first wire 150 electrically coupled to the top of the transducer 105 through the matching layer 135 and second wire 155 electrically coupled to the bottom of the transducer 105 through a conductive epoxy 160 and the conductive backing layer 140. The first wire 150 is attached to the matching layer 135 by a solder bump 165 or other conductive adhesive. The second wire 155 is encased in the conductive epoxy 160 which forms a conduction path to the conductive backing layer 140. The first wire 150 and the transducer 105 are encased in a non-conductive epoxy, which prevents the top and bottom terminals of the transducer 105 from shorting out. The conductive epoxy 160 electrically couples the second wire to the metal transducer housing 115, which acts as a electrical ground. The conductive and non-conductive epoxy 160, 170 help hold the transducer assembly in place in the transducer housing 115. As shown in FIG. 5, the transducer assembly is fitted between two side walls 117 of the transducer housing 115.

Referring to FIGS. 7-10, the telescope assembly 30 comprises a male telescoping tube 220, a female telescoping tube 215, and a hub 225 attached to distal end of the female telescoping tube 220. The male telescoping tube 220 is adapted to be slidably received within the female telescoping tube 215. The hub 225 has a strain relief 230 in the form of a helical section that provides a gradual decrease in stiffness toward the distal end of the strain relief 230.

Figure 9:
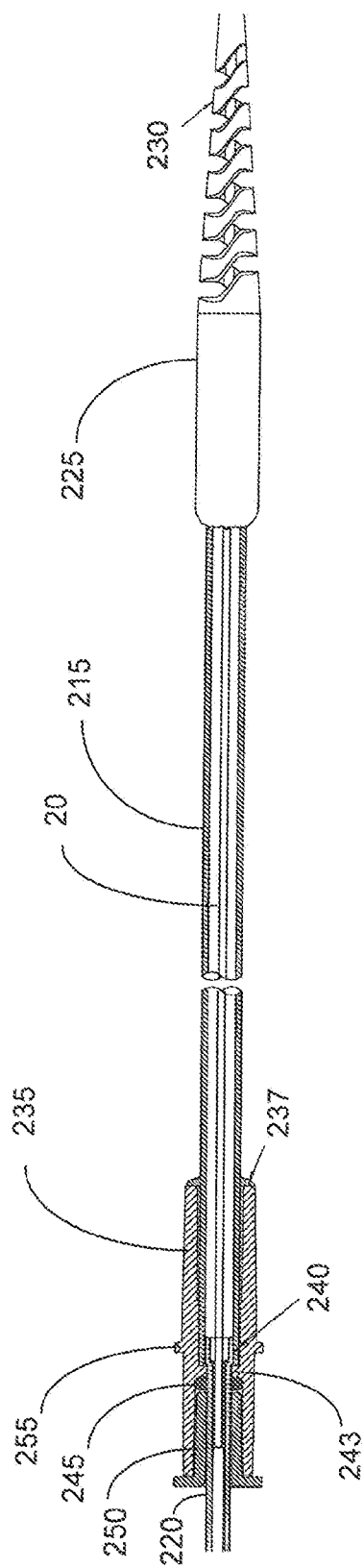
FIGS. 9 and 10 show cross-sectional views of the telescope assembly according to an example embodiment of the present invention.
Figure 10:
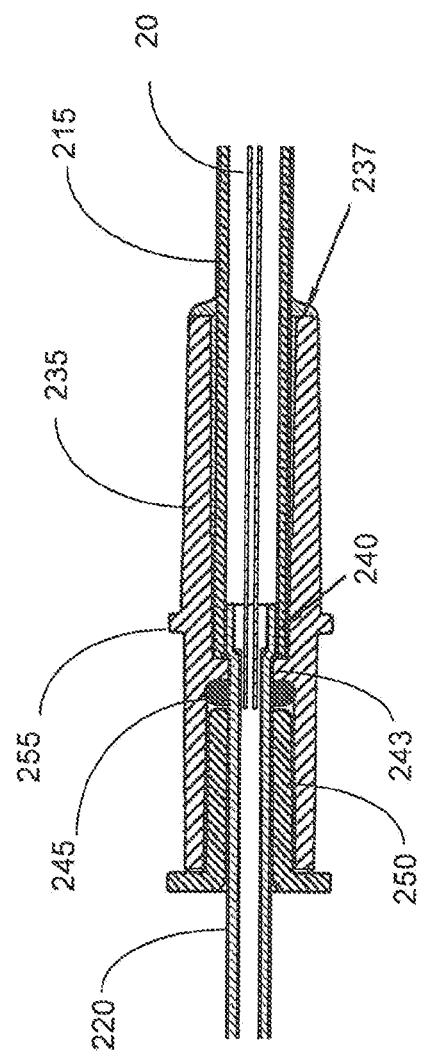

The telescope assembly 35 further comprises a telescope housing 235 that slidably couples the male telescoping tube 220 to the female telescoping tube 215. Referring to FIGS. 9 and 10, the telescope housing 235 comprises a lumen into which a proximal portion of the female telescoping tube 215 is inserted. The proximal portion of the female telescoping tube 215 is bonded to the telescope housing 235, e.g., using a UV activated adhesive. The male telescoping tube 210 passes through the lumen of the telescope housing 235 and comprises a flared portion 240 at its distal end. The mate telescoping tube 220 is adapted to slide through the lumen of the telescope housing 235 and into the female telescoping tube 215. The telescope housing 235 includes a stop member 243 that engages the flared portion 240 of the male telescoping tube 220 when the telescope assembly is fully extended to prevent the male telescoping tube from being pulled out of the telescope housing 235. The telescope housing 235 further comprises an o-ring 245 and a ring seal 250 that provide a sliding seal between the male telescoping tube 220 and the housing 235. The o-ring 245 is seated in the lumen between the stop member 243 and the seal 250. The outer surface of the ring seal 250 is bonded to the lumen by an adhesive 253 shown in FIG. 8. The o-ring 245 may be made with an elastomeric material such as silicon or rubber.

The proximal portion of the catheter sheath 20 extends through the hub 225 and into the female telescoping tube 215 as shown in FIGS. 9 and 10. In one embodiment, the proximal portion of the catheter sheath 20 extends the entire length of the female telescoping tubing 215 and into a distal portion of the male telescoping tube 220. The male telescoping tubing 220 is dimensioned to slide over the catheter sheath 20. Thus, the male telescoping tube 220 slides between the female telescoping tube 215 and the catheter sheath 20 to retract and extend the telescope assembly 30. The outer surface of the catheter sheath 20 is preferably bonded to the hub 225, e.g., using epoxy. In one embodiment, the imaging core 35 is placed in the sheath 20 before the sheath 20 is bonded to the hub 225. In this embodiment, the sheath 20 is moved to a desired position relative to the imaging core 35, at which point the sheath 20 is bonded to the hub 225. This method of assembly facilitates accurate positioning of the sheath 20 relative to the imaging core 35.

The portion of the catheter sheath 20 extending into the female telescoping tube 215 provides enhanced support for the drive cable 110 of the imaging core 35 within the female telescoping tube 215. Without the portion of the catheter sheath 20 extending into the female tube 225, the drive cable 110 would lie unsupported in the female telescoping tube 225 when the telescope assembly is in the fully extended position. The enhanced support provided by the portion of the catheter sheath 20 within the female telescoping tube 215 prevents wind-up and kinking of the drive cable 110.

Figure 11:
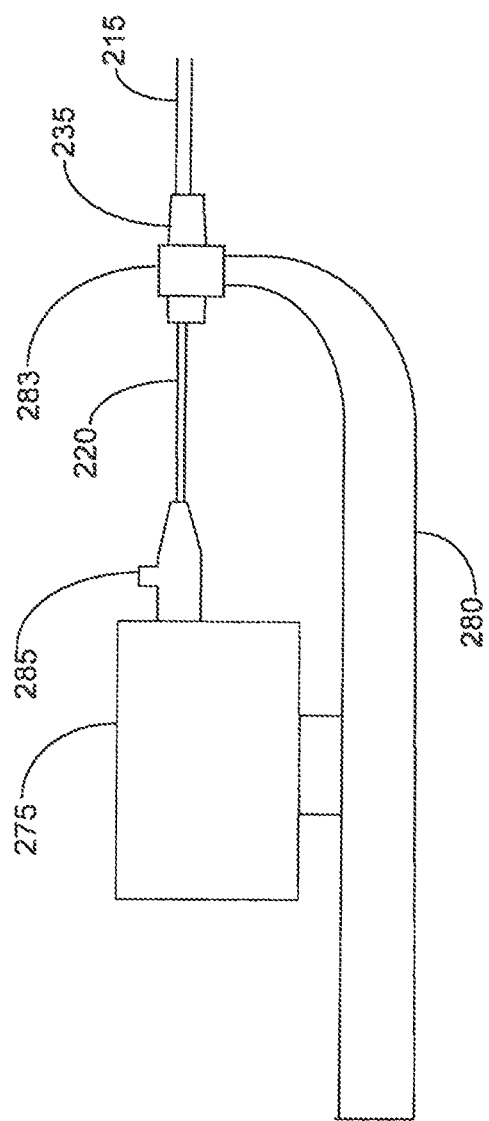
FIG. 11 shows the catheter coupled to a catheter drive system according to an example embodiment of the present invention.

The telescope housing 235 includes a notch 255 around the outer circumference of the housing 235. The notch 255 snaps onto a clip of a catheter drive system, an example of which is shown in diagram form in FIG. 11. The exemplary catheter drive system comprises a sled 280, a drive unit 275 that moves longitudinally along the sled 280, and a clip 283 at the distal end of sled 280. The clip 283 is adapted to engage the notch 255 of the telescope housing 235 to anchor the telescope housing 235 to the sled 280. Because the female telescoping tube 215 is attached to the telescope housing 235 and the catheter sheath 20 and the female tube 215 are both attached to the hub 225, anchoring the telescope housing 235 to the sled 280 also anchors the female tube 215 and sheath 20 to the sled 280. The male telescoping tube 220 and the drive cable 110 of the imaging core 35 are mechanically coupled to the drive unit 275, e.g., by a hub connector (not shown). The drive unit 275 is used to translate the male telescoping tube 220 and the imaging core 35 longitudinally relative to the catheter sheath 20, which is anchored to the sled 280. The drive unit may 275 include a translator drive motor (not shown) for translating the drive unit longitudinally, and a rotary drive motor (not shown) for rotating the imaging core within the catheter body. As shown in FIG. 11, the catheter system may include a flush port 285 for delivering fluid into the catheter sheath lumen, e.g., during a flushing procedure. Further details of catheter drive systems can be found, for example, in U.S. Pat. No. 6,398,755, titled "Driveable Catheter System," issued on Jun. 4, 2002, the specification of which is incorporated by reference.

During an operation, the catheter 10 is advanced, e.g., through the radial artery, to a desired site in the patient's vascular system. In one embodiment, the catheter 10 is advanced through a guide catheter (not shown) to the desired site. After the catheter 10 and imaging core 35 are positioned at the desired site, the catheter sheath 20 is anchored (locked) to the sled 280. Preferably the imaging core 35 is positioned distally within the catheter sheath 20 and the telescope assembly is in a retracted state. The short guidewire receiver 50 enables the imaging core 35 to be positioned closer to the distal end of the catheter 10, and therefore farther into the patient's vascular system. After the catheter sheath 20 is locked in place, the imaging core 35 is rotated to obtain radial cross-sectional images of the site. In addition, the male telescoping tube 220 and imaging core 30 are pulled back by the drive unit 275. This extends the telescope assembly and moves the imaging core 35 longitudinally within the sheath 20 allowing the image core 35 to obtain radial cross-section images at different potions along a length of the desired site. These cross-sectional images can be aggregated by an ultrasound processor into a three dimensional image.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed:

1. An intravascular catheter, comprising:
   a catheter sheath having a main portion, a distal portion, and a tapered portion located between the main portion and the distal portion, wherein the tapered portion has a wall thickness that gradually decreases in a direction toward the distal portion of the catheter sheath, the catheter sheath comprising a lumen configured and arranged for receiving an imaging core, the lumen extending to the distal portion of the catheter sheath, wherein the distal portion of the catheter sheath has an angled distal region;
   a guidewire receiver attached to the distal portion of the catheter sheath and extending distally beyond the distal portion of the catheter sheath and beyond the lumen of the catheter sheath, the guidewire receiver comprising a lumen for receiving the guidewire and an opening for insertion of a guidewire into the guidewire receiver from an exterior of the intravascular catheter, wherein the guidewire receiver has an angled proximal portion attached to, and overlapping with, the angled distal region of the distal portion of the catheter sheath; and
   a telescoping assembly attached to a proximal portion of the catheter sheath.

2. The catheter of claim 1, wherein the tapered portion of the catheter sheath has a maximum outer diameter of less than 0.045 inches.

3. The catheter of claim 1, wherein the guidewire receiver has a length of 20 millimeters or less.

4. The catheter of claim 1, wherein a region within which the angled proximal portion of the guidewire receiver attaches to the angled distal region of the distal portion of the catheter sheath has a substantially uniform outer diameter.

5. The catheter of claim 1, wherein a longitudinal axis of the guidewire receiver is at an angle with respect to a longitudinal axis of the catheter sheath.

6. The catheter of claim 5, wherein the angle is between 5 and 10 degrees.

7. The catheter of claim 5, wherein the guidewire receiver has an outer diameter of 0.045 inches or less.

8. The catheter of claim 1, further comprising an imaging core received within a lumen of the catheter sheath.

9. The catheter of claim 1, wherein the telescope assembly comprises:
   a female telescoping tube; and
   a male telescoping tube adapted to slide within the female telescoping tube;
   wherein a proximal portion of the catheter sheath extends into the female telescoping tube, and the male telescoping tube is adapted to slide over the proximal portion of the catheter sheath.

10. The catheter of claim 9, wherein the proximal portion of the catheter sheath extends through the female telescoping tube and into a distal portion of the male telescoping tube when the telescope assembly is in a fully extended state.

11. The catheter of claim 10, further comprising an imaging core extending through the male telescoping tube and a lumen of the catheter sheath.

12. The catheter of claim 9, wherein the telescope assembly further comprises a telescope hub, wherein a distal portion of the female telescoping tube is attached to the hub, and the proximal portion of the catheter sheath extends through the hub into the female telescoping tube.

13. The catheter of claim 12, wherein the proximal portion of the catheter sheath and a portion of the catheter sheath extending distally from the hub comprise a single continuous tubular piece.

14. The catheter of claim 1, wherein a joint, formed by overlapping the angled distal region of the catheter sheath with the angled proximal portion of the guidewire receiver, has a longitudinal axis that is angled with respect to a longitudinal axis of the catheter sheath.

15. The catheter of claim 1, wherein the angled distal region of the distal portion of the catheter sheath is tapered and the angled proximal portion of the guidewire receiver is tapered, wherein the angled distal region of the catheter sheath is bonded to the angled proximal portion of the guidewire receiver.

16. The catheter of claim 15, wherein the catheter sheath comprises a longitudinal axis and wherein the guidewire receiver is attached to the catheter sheath at a non-zero angle to the longitudinal axis of the catheter sheath.

17. The catheter of claim 16, wherein the non-zero angle is at least 6 degrees and less than 10 degrees.

18. The catheter of claim 15, wherein the angled distal region of the catheter sheath is tapered upward and the angled proximal portion of the guidewire receiver is tapered downward.

19. The catheter of claim 1, wherein the tapered portion has a length in a range of 10 to 20 centimeters.

* * * * *